United States Patent [19]

Haesen

[11] Patent Number: 4,502,330

[45] Date of Patent: Mar. 5, 1985

[54] PULSE-ECHO SYSTEM FOR MEASURING PARAMETERS OF A TUBULAR TEST OBJECT

[75] Inventor: Wilhelmus M. J. Haesen, Dordrecht, Netherlands

[73] Assignee: B.V. Neratoom, The Hague, Netherlands

[21] Appl. No.: 427,570

[22] Filed: Sep. 29, 1982

[30] Foreign Application Priority Data

Oct. 5, 1981 [NL] Netherlands ............... 8104526

[51] Int. Cl.³ ............................................. G01N 29/00
[52] U.S. Cl. ................................................. 73/623
[58] Field of Search ............... 73/622, 623, 629, 637, 73/638; 367/151

[56] References Cited

U.S. PATENT DOCUMENTS 4,022,055  5/1977  Flournoy et al. ............... 73/622
4,201,971  5/1980  Saglio ............................ 367/151
4,361,044  11/1982  Kupperman et al. ............ 73/623

Primary Examiner—Stephen A. Kreitman
Assistant Examiner—John E. Chapman, Jr.

[57] ABSTRACT

A system for improving the pulse-echo type of testing to determine certain parameters of tubes, such as internal diameter, external diameter, wall thickness, etc. A pair of pulses are directed transversely to the tube wall so that the transit times of the respective pulses and their reflections from a tube surface, are substantially different. From the value of the transit times associated with each pulse pair the respective parameter is derived. Inaccuracies due to undesired oscillations of the driving shaft for rotating the pulse transducer within the tube to be tested are eliminated. By means of auxiliary reflective surfaces each pair of pulses emitted from the transducer are directed transversely relative to the respective tube wall in substantially one and the same plane.

6 Claims, 3 Drawing Figures

PULSE-ECHO SYSTEM FOR MEASURING PARAMETERS OF A TUBULAR TEST OBJECT

This invention relates in general to a system for measuring parameters of a pipe-shaped or tubular test object. For the determination of relevant parameters of such a test object, such as outer diameter, inner diameter, wall thickness, ellipticity, and eccentricity, use is made in general of a pulse-echo technique, in which the desired parameters can be calculated from travel periods of echo pulses arising as a result of measurement signal pulses transmitted to the object being measured.

The invention relates in particular to a measurement system designed to perform the above measurements from the interior of pipe-shaped or tubular test objects of relatively small diameters. It is then a requirement for the transducer for the transmission of measurement signal pulses, e.g. ultrasound pulses, to the test object, or for receiving echo signal pulses arising from reflections against the object being measured, to fit in the object being measured together with the holder serving for the transducer. According to one proposed solution, the transducer is in such a system arranged to transmit and receive signals in the axial direction, there being employed a reflector rotatable about the main axis of the transducer, and positioned at a certain angle, generally 45°, relative to the main axis.

Such a configuration, however, has the disadvantage that the accuracy of the measurements depends greatly on the degree to which the axis of rotation of the reflector and the main axis of the transducer coincide. As a result of oscillations of the axis of rotation of the reflector relative to the main axis of the transducer, and hence relative to the axis of the object being measured, the measurements regarding the outer diameter, inner diameter, ellipticity, and eccentricity can no longer be unambiguously defined, as the reference i.e., the axis of the object being measured, apparently moves relatively to the transducer. Owing to the unbalance of the reflector, the effect of undesirable vibrations is reinforced still further, which additionally detracts from the accuracy of the measurements.

It is an object of the present invention to eliminate the disadvantages outlined above, and to make it possible to measure, in one and the same sectional plane of a pipe-shaped or tubular test object, the travel periods required for determining the desired parameter.

The present invention accordingly provides a system for measuring parameters of a pipe-shaped or tubular test object by means of a transducer for transmitting measurement signals to the test object and for receiving echo signals reflected by the test object, and also by means of a first and singular reflector positioned in opposition to said transducer and said test object, whereby measurement and echo signals are directed to travel in a pre-determined sectional plane of the test object, and between the transducer and the test object are guided along a first transmission path. The invention is characterized by a second and composite reflector, whereby measurement and echo signals are also directed to travel in said sectional plane of the test object and between the transducer and the test object are guided along a second transmission path. The transmission length of the second transmission path is so much longer than that of the relevant first transmission path that the difference between the two time intervals of a measurement signal transmitted to the test object and the first echo signal complex received via the relevant first transmission path, and the second echo signal complex received via the relevant second transmission path, is so great that these two echo signal complexes do not influence one another.

By adding up, in each case, the travel periods of the relevant echo pulses as determined by the first transmission path and the second transmission path, for example, the measurement of the inner diameter becomes independent of the oscillations of the transducer holder. In fact, if this transducer holder moves towards one side, the relevant travel period for that one side is decreased by an increment δ, whereas the travel period measured for the other side is increased by the same increment. The sum of the travel periods thus measured is then independent of the position which the transducer holder occupies relatively to the axis. The same applies to measurements regarding the outer diameter, ellipticity, and eccentricity. A second advantage is that the measuring velocity, i.e. the amount of data acquired per unit of time, determined by the wall thickness measurement, can be increased by a factor 2.

A preferred embodiment of a system according to the present invention is further characterized in that the singular reflector comprises a reflector surface facing the transducer, and disposed at a predetermined angle, preferably 45°, relative to the main axis of the transducer, and the composite reflector comprises a reflector surface facing away from the transducer, and disposed at a pre-determined angle relative to the main axis of the transducer.

A simple embodiment is characterized, according to the invention, in that the composite reflector comprises an auxiliary reflector surface facing the transducer and disposed at such an angle to the main axis of the transducer and that of said reflector surface facing away from said transducer, that the relevant second transmission path is composed of three rectilinear segments.

Another embodiment of the invention is characterized in that the composite reflector further comprises an auxiliary reflector surface facing said transducer and an auxiliary reflector surface facing said reflector facing away from said transducer, which two auxiliary reflector surfaces are so disposed relative to said transducer and said reflector surface facing away from said transducer that the relevant second transmission path is composed of four rectilinear segments.

Inaccuracies in measurements introduced by vibrations of the transducer holder can be fully eliminated if the system according to the invention is characterized in that said first reflector and said composite reflector are so disposed relative to each other that a measurement signal pulse generated by the transducer is transmitted to the test object in two diametrical and opposite directions.

A compact and simple embodiment is characterized according to the invention in that said first reflector and said composite reflector are bodily rotatable about the main axis of the transducer.

In order to further increase the measuring velocity, it is further of advantage to combine a plurality of systems of the embodiments described hereinbefore.

In further illustration of the invention, some embodiments thereof will be described hereinafter by way of example with reference to the accompanying drawings, in which.

Figure 1:
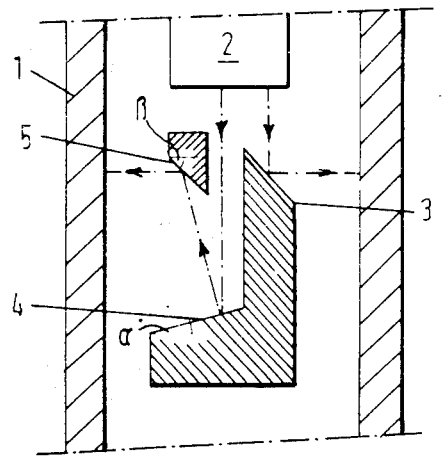
FIG. 1 is a diagrammatic illustration of a first embodiment of a measurement system according to the invention.

In FIG. 1 a portion of a pipe-shaped test object, of which the relevant parameters must be measured from the inside, is illustrated in cross-section and designated by 1. Diagrammatically shown at 2 is a holder with a transducer therein for transmitting measurement signals, in particular measurement signal pulses, to the test object, in particular the wall of pipe section 1, and for receiving echo signals, in particular echo signal pulses, reflected by the wall of pipe section 1. This holder/transducer is placed in the interior of pipe section 1 in such a manner that its geometrical main axis substantially coincides with the axis of pipe section 1. Furthermore, the transducer is arranged to transmit and receive a beam of measurement signals and echo signals, respectively, corresponding to the cross-section thereof.

Disposed in opposition to the transducer is a first reflector face 3 facing the same, whereby a measurement signal transmitted from the transducer is deflected with a given angle, in the embodiment shown, 90°, into the direction of the wall of pipe section 1. This first and singular reflector surface defines between the transducer and the wall of pipe section 1 a first transmission path via which a measurement signal wave, in particular the measurement signal pulse, transmitted from the transducer, extending in a cross-sectional plane of pipe section 1, is directed to the wall of this pipe section. There is furthermore provided in opposition to the transducer a second and composite reflector comprising an auxiliary reflector surface 4 facing the transducer and a reflector surface 5, the reflector surface 4 being positioned at such an angle to the geometrical longitudinal axis of the holder/transducer that a measurement signal wave, in particular the measurement signal pulse falling from the transducer on this auxiliary reflector surface is reflected to reflector surface 5. This reflector surface 5 is so disposed relative to reflector surface 3 and transducer 2 that a measurement signal wave coming from auxiliary reflector surface 4 falls on surface 5 in the same cross-sectional plane of pipe section 1, and is directed to the inner wall of this pipe section.

The auxiliary reflector surface 4 and reflector surface 5 define a second transmission path composed of three rectilinear segments. If now, a measurement signal pulse is transmitted from transducer 2, an echo pulse caused by reflection against the inner wall of the pipe section 1 will be received by the transducer via the above first transmission path, for example, after an interval $t_1$. An echo pulse caused by reflection against the inner wall and reaching the transducer via the above second transmission path will be received by the transducer, e.g. after an interval $t_2$. The sum of the time intervals $t_1$ and $t_2$ is a measure for the interior diameter of pipe section 1. Care has been taken, by correctly dimensioning the reflector composed of auxiliary reflector surface 4 and reflector surface 5, that the time interval $t_2$ is relatively long relative to time interval $t_1$. The difference between the two time intervals of a measurement signal transmitted to the test object and the first echo signal complex received via the relevant first transmission path, and the second echo signal complex received via the relevant second transmission path, is so great that these two echo signal complexes do not influence one another. An echo signal complex is a set of echo signals as caused by a transmitted measurement signal, and this set comprises a front wall echo and a plurality of rear wall echoes. In order to achieve that the measurement signal beams from reflector surfaces 3 and 5 are directed to extend in the same cross-sectional plane of the pipe section, the positional angle $\beta$ of reflector surface 5 equals 45°—$\alpha$, in which $\alpha$ represents the angle which the auxiliary reflector surface 4 encloses with the relevant cross-sectional plane through the pipe section 1. In a practical embodiment, reflector surfaces 3 and 5, and also auxiliary reflector surface 4 are combined to form one whole, which is bodily rotatable about the geometrical longitudinal axis of the transducer. In this arrangement, reflector surface 3 and the composite reflector are so positioned relative to each other that the measurement signal waves from reflector surfaces 3 and 5 are directed diametrically and in opposite directions to the wall of pipe section 1.

Naturally such an arrangement also permits measuring the echo signal caused by reflections against the external wall of pipe section 1, the time intervals measured for the first and the second transmission path being, respectively, $t_2$ and $t'_2$. Here too, the outer diameter of the pipe section can be determined by any summation of measured time from intervals $t_2$ and $t'_2$ without the accuracy of measurement being adversely affected by vibrations of the transducer. The other parameters, such as ellipticity, eccentricity and wall thickness, can also in principle be determined using the time intervals to be measured, such as $t_1$, $t'_1$, $t_2$ and $t'_2$.

Figure 2:
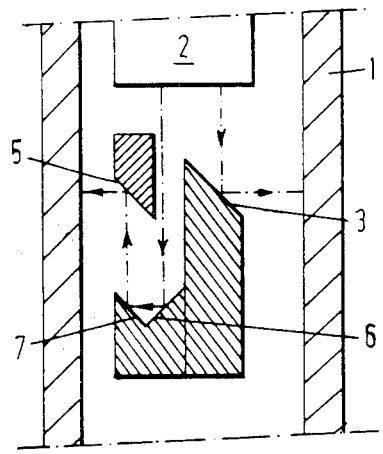
FIG. 2 is a diagrammatic illustration of a different embodiment of a measurement system according to the invention.

Of the configurations shown in FIG. 2, parts having a counterpart in the configuration illustrated in FIG. 1, are designated by the same reference numerals. The embodiment of FIG. 2 is only different from that of FIG. 1 in that, instead of a single auxiliary reflector surface, use is made of a pair of auxiliary reflector surfaces 6 and 7, disposed at an angle to each other. In this embodiment according to FIG. 2, a second transmission path is composed of four rectilinear segments. For the rest, the embodiments of FIGS. 1 and 2 are identical as far as operation is concerned.

For the sake of completeness, it is noted that, if ultrasound pulses are used for the measurement signal, the pipe to be tested is filled with a coupling fluid, such as water.

Figure 3:
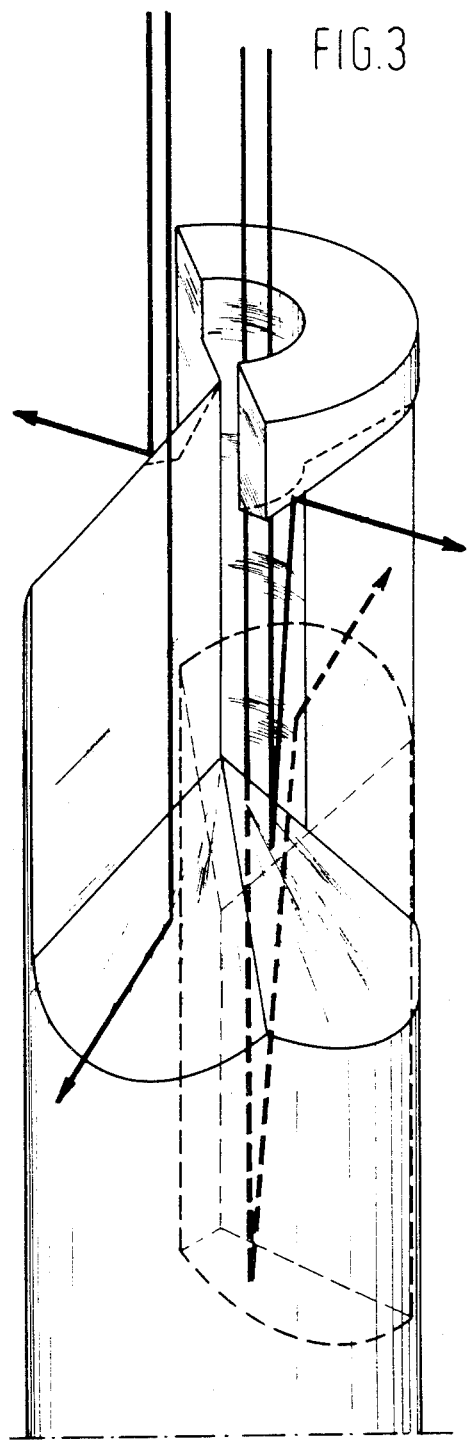
FIG. 3 is a diagrammatic illustration of an embodiment of the invention designed to increase the measurement velocity.

By combining a plurality of the reflector assemblies of FIGS. 1 and 2 to form one whole by means of multiple facet mirrors, the measuring velocity can be increased. FIG. 3 diagrammatically illustrates how, in this way, two sets of diametrically and oppositely directed signal waves can be produced. In this way the measuring velocity can be further increased by a factor 2. Naturally, with a larger number of facets, the measuring velocity can be correspondingly increased. According to the invention it is thus possible to carry out the measurements of the relevant parameters (dimensions) of a pipe-shaped or tubular test object without the problem of pulse interference, and without the accuracy of the measurements being adversely affected by the relative movement of the transducer holder relative to a reference, such as the axis of the pipe. With each measurement, the parameters such as outer diameter, inner diameter, ellipticity, eccentricity and wall thickness can be derived.

I claim:

1. A system for testing a pipe-shaped or tubular set object, comprising: a transducer for transmitting test signal waves to an inner wall of said test object and for receiving echo signal waves reflected from the inner wall, said transducer having a main axis; a first reflector disposed opposite to said transducer and the inner wall for causing test signal waves and echo signal waves to propagate in a predetermined sectional plane of said test object along a first transmission path between said transducer and said test object, a second reflector for causing test signal waves and echo signal waves to propagate along a second transmission path between said transducer and said inner wall; and a third reflector facing away from said transducer and disposed in said second transmission path between said second reflector and said inner wall; said second reflector being disposed at such an angle relative to the main axis of the transducer and to said third reflector that said second transmission path is composed of at least three rectilinear segments; the length of said second transmission path being sufficiently greater than the length of said first transmission path that the difference between the time intervals of a test signal wave transmitted to the inner wall and a first echo signal wave complex received from said inner wall by said transducer via said first transmission path, and a second echo signal wave complex received from said inner wall by said transducer via said second transmission path, is of such magnitude that said two echo signal wave complexes have no influence on each other.

2. A system for testing a pipe-shaped or tubular test object, comprising: a transducer for transmitting test signal waves to an inner wall of said test object and for receiving echo signal waves reflected from the inner wall, said transducer having a main axis; and a plurality of reflector assemblies; each reflector assembly having a first reflector disposed opposite to said transducer and the inner wall for causing test signal waves and echo signal waves to propagate in a predetermined sectional plane of said test object along a first transmission path between said transducer and said test object, a second reflector for causing test signal waves and echo signal waves to propagate along a second transmission path between said transducer and said inner wall; and a third reflector facing away from said transducer and disposed in said second transmission path between said second reflector and said inner wall; said second reflector being disposed at such an angle relative to the main axis of the transducer and to said third reflector that said second transmission path is composed of at least three rectilinear segments; the length of said second transmission path being sufficiently greater than the length of said first transmission path that the difference between the time intervals of a test signal wave transmitted to the inner wall and a first echo signal wave complex received from said inner wall by said transducer via said first transmission path, and a second echo signal wave complex received from said inner wall by said transducer via said second transmission path, is of such magnitude that said two echo signal wave complexes have no influence on each other.

3. A system according to claim 1 or 2, wherein said second reflector comprises a pair of reflector surfaces each disposed at such an angle that said second transmission path is composed of four rectilinear segments.

4. A system according to claim 1 or 2, wherein said first reflector and said third reflector are disposed relative to the main axis of said transducer so that a test signal wave generated by said transducer propagates to said inner wall along two diametrical and opposite directions.

5. A system according to claim 3, wherein said first reflector and said third reflector are disposed relative to the main axis of said transducer so that a test signal wave generated by said transducer propagates to said inner wall along two diametrical and opposite directions.

6. A system according to claim 1 or 2, wherein said first reflector, said second reflector, and said third reflector form a structural unit which is mounted for rotation relative to the main axis of said transducer.

* * * * *